United States Patent [19]

Contamin

[11] Patent Number: 4,543,205
[45] Date of Patent: Sep. 24, 1985

[54] COSMETIC CLEANSING COMPOSITION PARTICULARLY FOR REMOVAL OF EYE MAKE-UP

[75] Inventor: Jean-Claude Contamin, Chilly Mazarin, France

[73] Assignee: Societe Anonyme dite: L'Oreal, Paris, France

[21] Appl. No.: 664,730

[22] Filed: Oct. 25, 1984

[30] Foreign Application Priority Data

Oct. 25, 1983 [FR] France ................. 83 16978

[51] Int. Cl.$^4$ ................. C11D 1/84; C11D 1/831
[52] U.S. Cl. ................. 252/546; 252/106; 252/174.17; 252/174.23; 252/174.24; 252/542; 252/551; 252/DIG. 5; 252/DIG. 14
[58] Field of Search ............. 252/106, 174.17, 174.24, 252/542, 546, 174.23, 551, DIG. 5, DIG. 13, DIG. 14

[56] References Cited

U.S. PATENT DOCUMENTS

| | | | |
|---|---|---|---|
| 2,974,134 | 3/1961 | Pollitzer ................. | 252/174.17 X |
| 3,598,865 | 8/1971 | Lew ................. | 252/174.17 X |
| 3,708,435 | 1/1973 | Starkman ................. | 252/544 |
| 3,962,418 | 6/1976 | Birkoffer ................. | 424/70 |
| 4,231,903 | 11/1980 | Lindemann et al. ................. | 252/548 |

FOREIGN PATENT DOCUMENTS

| | | | |
|---|---|---|---|
| 24031 | 2/1981 | European Pat. Off. ....... | 252/174.21 |
| 28297 | 3/1981 | Japan ................. | 252/542 |
| 89697 | 5/1983 | Japan ................. | 252/546 |

*Primary Examiner*—Prince E. Willis

[57] ABSTRACT

A cosmetic cleansing composition capable of removing eye make-up comprises in an aqueous solution a cleansing agent comprising a mixture of surface active agents in the indicated amounts:

(i) from 0.1 to 2 percent by weight, based on the total weight of said composition, as active material, of a glucoside alkylether having the formula $$\text{(I)}$$

(structure shown with two glucose units with $CH_2OH$, $OH$ groups and $OR$ terminus, subscript $n$)

wherein
R represents alkyl having 8–12 carbon atoms,
n is equal to 0, 1, 2, 3, 4 or 5;

(ii) from 0.1 to 2 percent by weight, based on the total weight of said composition, as active material, of an amphoteric material of the formula $$R-\underset{\text{O}}{\overset{\|}{C}}-NH-(CH_2)_2-\overset{[\oplus]_n R'}{\underset{(CH_2)_y COONa}{N}}-(CH_2 COO^\ominus)_n \quad \text{(II)}$$

wherein
n is 0 or 1,
y is 1 or 2,
R represents a fatty chain having from 7 to 17 carbon atoms and
R' represents $-CH_2-CH_2OH$ or $-(CH_2)_2-O-(CH_2)_2-COONa$,
optionally in admixture with an oxyethylenated alkyl sulfate of the formula $C_{13}H_{27}-(OCH_2CH_2)_m-OSO_3Na$ wherein m is 1–4 (III); and (iii) from 0.3 to 5 percent by weight, based on the total weight of said composition, as active material, of a compound selected from the group consisting of (a) the monolaurate or the mono-oleate of sorbitan polyoxyethylenated with 20 moles of ethylene oxide,
(b) the monolaurate or the mono-oleate of glycerol polyoxyethylenated with 20 moles of ethylene oxide, and
(c) a non-ionic compound having the formula $$R-O-CH_2-CH-R' \atop \underset{}{\overset{}{O}}-\left[CH_2-CH-O\atop\underset{CH_2OH}{|}\right]_n-H \quad \text{(IV)}$$

wherein
R represents a fatty chain having 8–10 carbon atoms,
R' represents a fatty chain having 10–16 carbon atoms, and
n ranges from 10 to 12, the ratio $n/R+R'$ being between 0.4 and 0.6.

12 Claims, No Drawings

COSMETIC CLEANSING COMPOSITION PARTICULARLY FOR REMOVAL OF EYE MAKE-UP

The present invention relates to a new cosmetic cleansing composition, principally a make-up remover lotion for the eyes, exhibiting excellent make-up removal powder, good innocuousness in ocular testing, good cosmetic comfort and excellent preservation qualities, not only with respect to time but also to various storage temperatures.

There have already been proposed, in French Pat. Nos. 77.15292, 77.20116 and 77.39840, as well as in Certificate of Addition No. 79.14693 (Certificate of Addition to French Pat. No. 77.20116), various make-up remover lotions for the eyes in which the surface active agent is essentially constituted by (1) an alkyl or hydroxyalkyl polyglycoside wherein the alkyl radical has from 11 to 18 carbon atoms and wherein the number of glycoside units is between 3 and 25; or (2) the mono-laurate or mono-oleate of sorbitan oxyethylenated with 20 moles of ethylene oxide; or (3) an alkyl carboxylate of polyethoxylated α-methyl glucoside wherein the alkyl radical linear or branched, saturated or unsaturated, has from 12 to 22 carbon atoms; or (4) an ester of a fatty acid and polyoxyethylenated glycerol, the said fatty acid, saturated or unsaturated, having from 12 to 18 carbon atoms and the said ester having an HLB between 15 and 18.

These known lotions, based on these surface active agents, while exhibiting good make-up removal properties and being essentially free of any ocular difficulty that is to say irritation or stinging of the eyes, have been found to be nonetheless on the one hand, difficult to preserve over extended periods of time especially when the storage temperatures vary significantly and, on the other hand, they exhibit unsatisfactory cosmetic comfort qualities for this type of product, i.e. the lotions based on these surface active agents occasionally have a tendency to stick to the eyelashes and eyelids of the user.

An important criteria for these types of compositions is that they must be able to be used over long periods of time which requires that they exhibit excellent stability not only during storage but also over wide temperature ranges. In other words, these compositions must not give rise to disadvantages caused by the instability of certain ones of their components, principally the surface active agent(s) employed therein.

The present invention provides a new cosmetic cleansing composition, principally an eye make-up remover lotion whose cleansing agent is constituted by a mixture of surface active agents, this mixture having the single purpose of obtaining compositions exhibiting all the properties required for this type of product, that is to say, excellent make-up removal characteristics, good cosmetic comfort, good innocuousness in ocular testing and excellent long time preservation at widely varying temperatures.

The present invention thus relates to, as a new industrial product, a cosmetic cleansing composition, principally for eye make-up removal, containing in an aqueous solution, in addition to components conventionally employed in this type of composition, a cleansing agent constituted by a mixture of surface active agents in the following amounts:

(i) from 0.1 to 2 percent by weight, as active material, of a glucoside alkylether having the formula

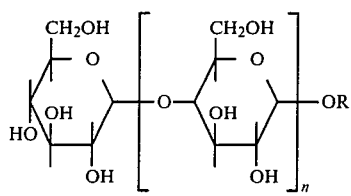

wherein R represents alkyl having from 8–12 carbon atoms and n is equal to 0, 1, 2, 3, 4 or 5;

(ii) from 0.1 to 2 percent by weight, as active material, of an amphoteric material having the formula

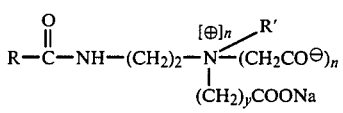

wherein n is 0 or 1; y is 1 or 2, R represents a fatty chain having from 7 to 17 carbon atoms, preferably 11 carbon atoms, and R' represents —CH$_2$—CH$_2$OH or —(CH$_2$)$_2$—O—(CH$_2$)$_2$—COONa, optionally in admixture with an oxyethylenated alkyl sulfate of the formula $$C_{13}H_{27}-(OCH_2CH_2)_m-OSO_3Na \quad \text{(III)}$$

wherein m is 1 to 4; and (iii) from 0.3 to 5 percent by weight, as active material, of a compound selected from the group consisting of (a) the monolaurate or mono-oleate of sorbitan polyoxyethylenated with 20 moles of ethylene oxide, (b) the monolaurate or mono-oleate of glycerol polyoxyethylenated with 20 moles of ethylene oxide, and (c) a non-ionic compound having the formula

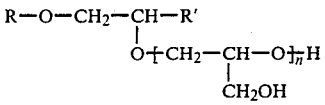

wherein

R represents a fatty chain having 8 to 10 carbon atoms,

R' represents a fatty chain having 10 to 16 carbon atoms, and n is between 10 and 12, the ratio, n/R+R' being between 0.4 and 0.6.

Various tests which have been carried out show that only the combination of these three surface active agents, in the amounts indicated above, is capable of providing all the desired properties of such a composition. The presence of the monolaurate or mono-oleate of polyoxyethylenated sorbitan, or glycerol, has been found to be indispensible in producing good long time stability of the composition, without observing the appearance of an irreversible cloudiness when the composition is submitted to a temperature lower than 10° C. and then brought back to ambient temperature.

In effect, when there is employed, as the cleansing agent only the combination of a glucoside alkylether of formula (I) and an amphoteric material of formula (II), or of either one alone in admixture with the compound of formula (III), the resulting cleansing composition, if it exhibits, after its preparation, good make-up removal and innocuousness characteristics, it fails rapidly on the other hand, to provide adequate stability characteristics which consequently renders it essentially useless or unacceptable.

In accordance with a preferred embodiment of the present invention, the cleansing agent comprises (i) 0.2 to 1.5 weight percent, as active material, of the glucoside alkylether of formula (I);

(ii) 0.2 to 1.5 weight percent, as active material, of the amphoteric material of formula (II), either alone or in admixture with the compound of formula (III); and (iii) 0.5 to 3 weight percent, as active material, of the monolaurate or mono-oleate of sorbitan or glycerol, polyoxyethylenated with 20 moles of ethylene oxide, or a nonionic compound of formula (IV).

Representative glucoside alkylethers of formula (I) include, in particular, those wherein the radical R represents $C_{12}H_{25}$ and n=5 or again those wherein the radical R represents a 50:50 $C_8$–$C_{10}$ mixture and n is equal to 0, as well as those wherein R has this same meaning and n is 1–4, and principally a commercial product sold by Rohm and Haas under the tradename "Triton CG. 110-30".

Representative amphoteric materials of formula (II) include, in particular, those sold by Miranol Chemical Company Inc., under the tradenames "Miranol C2M Conc", "Miranol C2M SF Conc", "Miranol 2 MCT MOD", "Miranol 2 MHT MOD" and "Miranol MHT".

Representative compounds of formula (III), optionally combined with the compounds of formula (II), include those sold by Miranol Chemical Company Inc. under the tradenames of "Miranol 2 MCT MOD", Miranol BT", "Miranol 2 MHT MOD", and "Miranol MHT".

The monolaurate of sorbitan polyoxyethylenated with 20 moles of ethylene oxide is more commonly known under the commercial designation "TWEEN 20" and the mono-oleate of sorbitan polyoxyethylenated with 20 moles of ethylene oxide is more commonly known under the commercial designation "TWEEN 80".

Although the mono-oleate of glycerol polyoxyethylenated with 20 moles of ethylene oxide leads to satisfactory results, there is preferably employed, according to the invention, the monolaurate of glycerol polyoxyethylenated with 20 moles of ethylene oxide sold under the tradename "TAGAT.L.2" by Goldschmidt.

Representative non-ionic compounds of formula (IV), include, in particular, those described in Belgium Pat. No. 885,269, principally those wherein R represents $C_8H_{17}$, R' represents $C_{14}H_{29}$ and n=12.

The vehicle or carrier for the cleansing compositions of the present invention is either sterile demineralized water or a floral water such as rose water, corn-flower water, camomile water or linden water.

The other components of the cleansing composition are essentially a preservative which can be, for example, sodium ethylmercurithiosalicylate, a chlorhexidine salt such as the digluconate, diacetate and dihydrochloride thereof, a phenylmercury salt such as phenylmercury nitrate, a mixture constituted by 30% sodium benzoate and 70% monochloracetamide, a compound having the formula

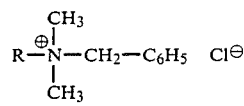

wherein R represents alkyl having 12–18 carbon atoms or a mixture of alkyl radicals such as $C_{12}$–$C_{14}$ mixtures and $C_{14}$–$C_{16}$ mixtures.

The preservative employed in the compositions of the present invention is generally used in an amount between 0.002 and 0.8 weight percent, preferably between 0.02 and 0.5 weight percent, based on the total weight of the composition.

The pH of the compositions according to the present invention is generally between 6.5 and 7.5, and preferably between 7 and 7.2. The pH is obtained using a buffer agent such as, for example, a phosphate buffer (dipotassium hydrogen phosphate/potassium dihydrogenphosphate).

The cleansing compositions according to the present invention can also contain a non-ionic or anionic polymer. It has been observed, in a quite surprising manner, that when there is employed, in the cleansing compositions of this invention, a non-ionic or anionic polymer in an amount between 0.1 and 3 weight percent based on the total weight of the composition, it is possible to reduce substantially the concentrations of the three surface active agents without otherwise influencing the properties of the composition, especially its cleansing power.

Representative non-ionic polymers that can be used in the compositions according to the present invention include:

(i) poly-$\beta$-alanines described in Belgium Pat. No. 208,516. These polymers have from 50 to 100% of repeating units of the formula

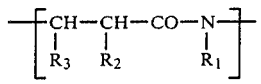

and from 0 to 50% of repeating units of the polyacrylamide type corresponding to the following formula

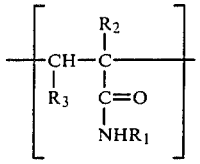

wherein $R_1$ represents hydrogen or a member selected from the group consisting of (i')

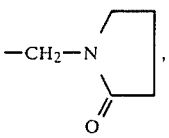

(ii') —$CH_2OH$, (iii') —$(CH_2)_{n'}$—$CH_3$ wherein n' is 0 or a whole number from 1 to 11, and (iv') —$(CH_2—CH_2—O)_m$—H, wherein m ranges from 1 to 10, and $R_2$ and $R_3$ represent hydrogen or methyl.

These polymers are prepared by polymerization of acrylamide, as described in U.S. Pat. No. 4,082,730. These polymers have, preferably, a molecular weight between 500 and 200,000 and more particularly between 2,000 and 100,000;

(ii) polyvinylpyrrolidone having a molecular weight between 10,000 and 400,000;

(iii) hydroxyethylcellulose, for example "NATROSOL 250" sold by Hercules; and (iv) hydroxypropyl derivatives of guar gum, in particular "JAGUAR H P-8" sold by Meyhall.

Representative anionic polymers, include in particular:

(i'') the copolymer of vinyl methyl ether and maleic acid obtained by hydrolysis of the corresponding anhydride copolymer, such as that sold by GAF Corp. under the commercial tradename "RESINE GANTREZ AN 119";

(ii'') sodium polymethacrylate such as that sold by Vanderbilt under the tradename "DARVAN 7"; and (iii'') polymers of acrylic acid such as those sold by Allied Colloids under the tradenames of "VERSICOL $E_5$" (mol.wt=2,500) or "VERSICOL $E_{11}$" (mol.wt=230,000).

The compositions according to the present invention can also contain other conventional adjuvants such as, for example, humectant agents, softening agents, perfumes or dyes, with the proviso, however, that these adjuvants are stable in the composition and do not cause any irritation or stinging of the ocular mucous.

Representative humectant agents include, in particular, hexylene glycol and polyethylene glycol 600.

Representative softening agents include, in particular, allantoin and azulene.

The following non-limiting examples are given to illustrate the cleansing compositions of the present invention.

EXAMPLE 1

An eye make-up remover lotion is prepared by admixing the following components:
Triton CG.110-30 (30% active material)—1 g
Miranol C2M—1 g
Tween 20—1 g
Allantoin—0.05 g
Hexylene glycol—2 g
Potassium dihydrogen phosphate—0.1 g
Dipotassium hydrogen phosphate—0.3 g
Benzalkonium chloride—0.25 g
Linden water—10 g
Perfume—0.1 g
Sterile demineralized water, amount sufficient for—100 g
This lotion has a pH of about 7.2

EXAMPLE 2

An eye make-up remover lotion in accordance with the present invention is prepared by admixing the following components:
Triton CG. 110-30 (30% active material)—0.5 g
Miranol C2M—0.5 g
Tween 20—0.5 g
Non-ionic poly-$\beta$-alanine—0.85 g
Allantoin—0.05 g
Hexylene glycol—2 g
Potassium dihydrogen phosphate—0.1 g
Dipotassium hydrogen phosphate—0.3 g
Sodium ethylmercurithiosalicylate—0.003 g
Corn-flower water—10 g
Perfume—0.1 g
Sterile demineralized water, amount sufficient for—100 g
This lotion has a pH of about 7.1

In this example the presence of poly-$\beta$-alanine permits, relative to Example 1, to reduce by half the concentration of the three surface active agents without noting any modification in the properties of the lotion, principally its make-up removal power.

EXAMPLE 3

An eye make-up remover composition in accordance with the present invention is prepared by admixing the following components:
Glucoside lauryl ether (Formula I wherein R=lauryl and n=5)—0.7 g
Miranol 2MHT MOD (modified)—0.5 g
Glycerol monolaurate polyoxyethylenated with 20 moles of ethylene glycol, sold under the tradename TAGAT L2—0.6 g
Versical E5-E11—0.3 g
Potassium dihydrogen phosphate—0.1 g
Dipotassium hydrogen phosphate—0.3 g
Sodium ethyl mercurithiosalicylate—0.003 g
Perfume—0.1 g
Water, sufficient amount for—100 g
This composition has a pH of about 7.

EXAMPLE 4

An eye make-up remover composition according to the present invention is prepared by admixing the following components:
Glucoside alkylether of Formula I wherein R=$C_8/C_{10}$ (1/1 mixture) and n=0—1.2 g
Miranol MHT—0.9 g
Tween 80—0.7 g
Potassium dihydrogen phosphate—0.1 g
Dipotassium hydrogen phosphate—0.3 g
Sodium ethyl mercurithiosalicylate—0.003 g
Perfume—0.1 g
Water, sufficient amount for—100 g
This composition has a pH of about 7.1.

EXAMPLE 5

An eye make-up remover lotion according to the present invention is prepared by admixing the following components:
Triton CG.110-30 (30% active material)—1 g
Miranol C2M—1 g
Nonionic compound of Formula IV wherein R=$C_8H_{17}$, R'=$C_{14}H_{29}$ and n=12—1.5 g
Allantoin—0.05 g
Hexylene glycol—2 g
Potassium dihydrogen phosphate—0.1 g
Dipotassium hydrogen phosphate—0.3 g
Benzalkonium chloride—0.25 g
Perfume—0.1 g
Water, sufficient amount for—100 g
This lotion has a pH of about 7.

What is claimed is:
1. A cosmetic cleansing composition capable of removing eye make-up comprising in an aqueous solution a cleansing agent comprising a mixture of surface active agents in the below indicated amounts:

(i) from 0.1 to 2 percent by weight, based on the total weight of said composition, as active material, of a glucoside alkylether having the formula

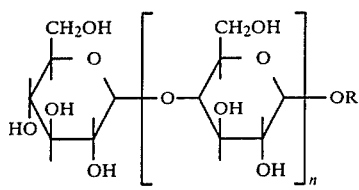

wherein R represents alkyl having 8-12 carbon atoms, and n is equal to 0, 1, 2, 3, 4 or 5;

(ii) from 0.1 to 2 percent by weight, based on the total weight of said composition, as active material, of an amphoteric material of the formula

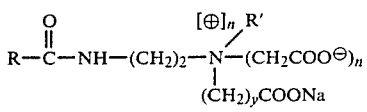

wherein
n is 0 or 1,
y is 1 or 2,
R represents a fatty chain having from 7 to 17 carbon atoms, and
R' represents $-CH_2-CH_2OH$ or $-(CH_2)_2-O-(CH_2)_2-COONa$,
optionally in admixture with an oxyethylenated alkyl sulfate of the formula $C_{13}H_{27}-(OCH_2CH_2)_m-OSO_3Na$ wherein m is 1-4 (III); and (iii) from 0.3 to 5 percent by weight, based on the total weight of said composition, as active material, of a compound selected from the group consisting of (a) the monolaurate or the mono-oleate of sorbitan polyoxyethylenated with 20 moles of ethylene oxide, (b) the monolaurate or the mono-oleate of glycerol polyoxyethylenated with 20 moles of ethylene oxide, and (c) a non-ionic compound having the formula

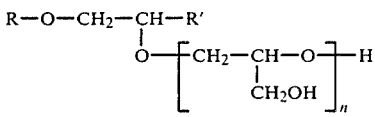

wherein
R represents a fatty chain having 8-10 carbon atoms,
R' represents a fatty chain having 10-16 carbon atoms, and
n ranges from 10 to 12, the ratio n/R+R' being between 0.4 and 0.6.

2. The composition of claim 1 wherein said cleansing agent comprises
(i) from 0.2 to 1.5 percent by weight, based on the total weight of said composition, as active material, of said glucoside alkylether of formula (I),
(ii) from 0.2 to 1.5 percent by weight, based on the total weight of said composition, as active material, of said amphoteric material of formula (II), alone or in admixture with said oxyethylenated alkyl sulfate of formula (III) and
(iii) from 0.5 to 3 percent by weight, based on the total weight of said composition of the monolaurate or monooleate of sorbitan or glycerol, each polyoxyethylenated with 20 moles of ethylene oxide, or of the said non-ionic compounds of formula (IV).

3. The composition of claim 1 which also contains an effective amount of a preservative selected from the group consisting of sodium ethyl mercurithiosalicylate, the digluconate, diacetate or dihydrochloride of chlorhexidine, phenyl mercury nitrate, a mixture consisting of 30 percent of sodium benzoate and 70 percent of monochloracetamide, and a compound of the formula

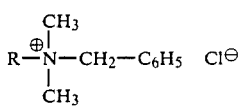

wherein R represents alkyl having 12-18 carbon atoms or a mixture of alkyl radicals selected from a $C_{12}-C_{14}$ mixture or a $C_{14}-C_{16}$ mixture.

4. The composition of claim 3 wherein said preservative is present in an amount ranging from 0.002 to 0.8 percent by weight based on the total weight of said composition.

5. The composition of claim 3 wherein said preservative is present in an amount ranging from 0.02 to 0.5 percent by weight based on the total weight of said composition.

6. The composition of claim 1 having a pH ranging from 6.5 to 7.5.

7. The composition of claim 1 having a pH ranging from 7 to 7.2.

8. The composition of claim 1 which also contains a non-ionic or anionic polymer.

9. The composition of claim 8 wherein said non-ionic or anionic polymer is present in an amount ranging from 0.1 to 3 percent by weight based on the total weight of said composition.

10. The composition of claim 8 wherein said non-ionic polymer is selected from a poly-$\beta$-alanine, polyvinylpyrrolidone, hydroxyethyl cellulose and a guar gum derivative.

11. The composition of claim 8 wherein said anionic polymer is selected from the copolymer of methyl vinyl ether and maleic acid, sodium polymethacrylate and an acrylic acid polymer.

12. The composition of claim 1 which also contains an effective amount of at least one of a humectant agent, a softening agent, a perfume or a dye.

* * * * *